United States Patent
Olsen

[11] Patent Number: 6,060,091
[45] Date of Patent: *May 9, 2000

[54] METHOD FOR TREATMENT OF POTATO PULP

[75] Inventor: Hans Sejr Olsen, Holte, Denmark

[73] Assignee: Novo Nordisk A/S, Bagsvaerd, Denmark

[*] Notice: This patent is subject to a terminal disclaimer.

[21] Appl. No.: 08/256,322

[22] PCT Filed: Jan. 28, 1993

[86] PCT No.: PCT/DK93/00028

§ 371 Date: Jul. 8, 1994

§ 102(e) Date: Jul. 8, 1994

[87] PCT Pub. No.: WO93/15615

PCT Pub. Date: Aug. 19, 1993

[30] Foreign Application Priority Data

Feb. 6, 1992 [DK] Denmark ............................. 0142/92

[51] Int. Cl.[7] .................................................. A23K 3/00
[52] U.S. Cl. .................................................... 426/53
[58] Field of Search ................................ 426/52, 53

[56] References Cited

U.S. PATENT DOCUMENTS

| | | | |
|---|---|---|---|
| 4,081,555 | 3/1978 | Sawhill | 426/2 |
| 4,478,854 | 10/1984 | Adler-Nissen et al. | 426/12 |
| 4,478,940 | 10/1984 | Adler-Nissen et al. | 435/209 |
| 4,481,284 | 11/1984 | Downs | 435/259 |
| 4,483,874 | 11/1984 | Olsen | 426/44 |
| 4,483,875 | 11/1984 | Dörreich | 426/52 |
| 4,784,860 | 11/1988 | Christensen et al. | 426/46 |
| 4,886,672 | 12/1989 | de Baynast de Septfontaines et al. | 426/48 |
| 5,573,795 | 11/1996 | Olsen | 426/53 |

FOREIGN PATENT DOCUMENTS 25 54 369 10/1977 Germany.
29 09 015 9/1980 Germany.

OTHER PUBLICATIONS

L. Slominska et al., Starch, vol. 39, No. 4, pp. 121–125, 1987.

G. Richter et al., Starch, vol. 35, No. 4, pp. 113–118, 1983.

Primary Examiner—Arthur L. Corbin
Attorney, Agent, or Firm—Steve T. Zelson, Esq.; Valeta Gregg, Esq.

[57] ABSTRACT

A method of making an animal fodder stabilized against microbial degradation, by jet-cooking potato pulp at a temperature of between about 125° C. and 140° C. for between about 20 to 100 seconds, cooling the jet-cooked potato pulp, and adding a cell-wall degrading enzyme to the cooled potato pulp in order to enzymatically degrade the cell walls in the potato pulp, wherein a fodder stabilized against microbial degradation is produced.

6 Claims, 4 Drawing Sheets

METHOD FOR TREATMENT OF POTATO PULP

BACKGROUND OF THE INVENTION

The invention comprises a method for treatment of potato pulp.

Potato pulp is a certain fraction which appears during the potato starch production. The disintegrated, clean potato chips are first introduced into a decanter, the supernatant therefrom being the fruit water, which is further processed; the residue is introduced into a centrifugal sieve, from which two fractions are taken out, i.e. the potato starch fraction and the potato pulp fraction.

This potato pulp fraction consists of arabino galactan, cellulose, pectin, protein and a small amount of starch, and it exhibits a strong water binding capacity. The potato pulp contains only 3–4% dry matter and exhibits a gelly consistency. If exposed to pressure the water content of the potato pulp can be raised to around 10%, and in that case the consistency is like the consistency of marzipan.

The potato pulp has posed a problem to the farmers and to industry. One possibility is discarding the potato pulp, due to the low nutritional value thereof, and in that case an environmental problem arises. Another possibility comprises that the farmer takes the potato pulp back to the farm, in that case, however, it has to be used very soon as a fodder in order to prevent putrefaction, and it can be used only for certain animals. Furthermore, potato pulp is only produced around 3 months a year, which means that the quality of a composed fodder will vary over the year, if potato pulp is used as a fodder ingredient. This is unwanted from the point of view of the fodder producers.

The purpose of the invention is the provision of a cheap and simple conversion of the potato pulp to a nutritionally valuable and stable fodder.

Surprisingly it has been found that this purpose can be achieved by a combination of a cooking and a treatment with a specially selected enzyme.

SUMMARY OF THE INVENTION

Thus, the method for treatment of potato pulp according to the invention is characterized by the fact that the potato pulp is first cooked, and subsequently, after proper cooling, exposed to an enzymatic degradation process by means of a cell wall degradation enzyme, and then, if necessary, preserved to a product, which exhibits microbial stability, in any conventional manner.

The cooking process comprises a heating to at least 100° C. for a time period of at least 5 minutes. "Proper cooling" is to be understood as cooling to a temperature, at which the enzyme or enzymes possess at least a reasonably good stability.

If the liquid product, which appears directly after the treatment with the cell wall degrading enzyme exhibits the necessary microbial stability for the intended use thereof, no preservation is needed. The preservation, if needed, may be a pasteurization, an addition of a preservation agent, or a concentration. The concentrate can either be a concentrated liquid with a content of dry matter of 50% w/w or above, or a particle shaped material, such as a powder or a granulate.

DETAILED DESCRIPTION

Figure 1:
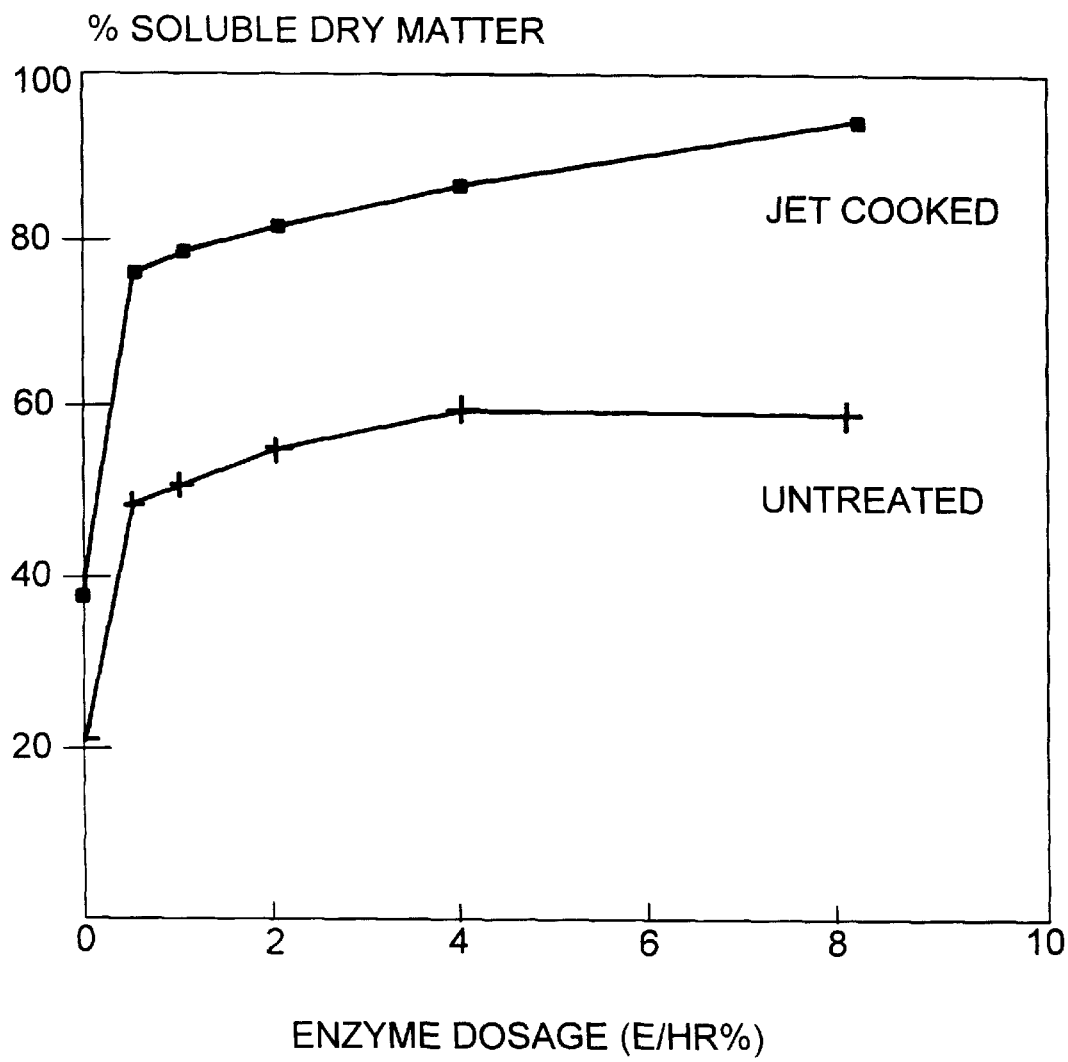
FIG. 1 shows percent soluble dry matter as a function of enzyme dosage for jet cooked and untreated samples described in Example 1.

It is described in Starch/Stärke 39 (1987) no. 4, p. 121–125 that potato pulp can be degraded by treatment with a cell wall degrading enzyme preparation, i.e. SP-249. However, as it clearly appears from FIG. 2 on page 123, the solid phase still constitutes a significant part of the degraded potato pulp, whereas according to the invention the potato pulp is practically completely solubilized. Due to the fact that the potato pulp according to the invention is practically completely solubilized, further processing thereof, especially separation, concentration or isolation of valuable components can easily be performed, in contradistinction to the prior art process. Also, the prior art product is not easily digestible, due to the solid phase, which mainly consists of unconverted polysaccharides.

The degraded potato pulp can be used directly as a juice, or it can be concentrated and evaporated to a syrup and finally spray dried. It has a good nutritional value, can be digested by all animals, and is bacteriologically stable. Also, besides being used as a fodder, it can be used as part of a fermentation substrate. Due to the fact that the potato pulp is practically completely solubilized, it can alternatively be mixed with the fruit water in the potato starch plant and further processed with the fruit water in the conventional manner.

The material which exits from the cooking, theoretically should not contain any starch, because the starch should have been separated from the pulp in the centrifugal sieve, as previously indicated. However, if small residues of starch are still present after the cooking, treatment with amylase is required directly after the cooking, i.e. simultaneously with the enzymatic degradation process, or immediately before or after the enzymatic degradation process, if the temperature or pH optima of the cell wall degradation enzyme and the amylase are too different.

In a preferred embodiment of the method according to the invention the cooking is a jet cooking, which is carried out at a temperature between 125 and 140° C., and for a time interval of between 20 and 100 seconds. Jet cooking is a special heat treatment in which efficient shearing and heating with direct steam is achieved with continuous flow through a combining tube. The trade mark of a typical jet cooker, which can be used in the method according to the invention is Hydroheater®, vide Example 3. If the temperature is above 140° C. and the time interval is above 100 seconds, the potato pulp will be burned, and if the temperature is less than 125° C. and the time interval is below 20 seconds, the subsequently performed enzymatic degradation will be insufficient. The higher the temperature, the smaller the time interval should be, and vice versa.

In a preferred embodiment of the method according to the invention is the enzymatic degradation process is carried out by means of SPS-ase. In this manner a satisfactory cell wall degradation is obtained. SPS-ase is described in e.g. GB2 115 820.

In a preferred embodiment of the method according to the invention the enzymatic degradation process is supported by means of cellulase and/or hemicellulase. In this manner an even better cell wall degradation is obtained.

In a preferred embodiment of the method according to the invention the temperature and pH-value is chosen in such manner that both the stability and the activity of the enzyme or enzymes are close to optimal values. In this manner the method can be carried out in a sound commercial manner.

In a preferred embodiment of the method according to the invention a preservation is carried out and the preservation comprises a concentration and a subsequent spray drying to a material with a water content of less than 5%. In this manner the most convenient product is obtained for transportation and later use as a fodder.

In a preferred embodiment of the method according to the invention the concentrate immediately before spray drying is mixed with potato fruit water, which has been jet cooked, enzyme treated and concentrated. In this manner both the potato pulp and the potato fruit water can be utilized as a fodder. Reference can be made to U.S. Pat. No. 5,573,795.

In a preferred embodiment of the method according to the invention the soluble part of the process stream between the enzymatic degradation process and the preservation process is exposed to an ultrafiltration process by means of an ultrafiltration equipment with a cut off value of around 20,000 Dalton. In this embodiment the permeate from the ultrafiltration process is processed according to the invention (i.e. preserved to a product, which exhibits microbial stability, in any conventional manner), whereas the retentate which contains a special product, i.e. "soluble potato fibre", which e.g. can be used as a fat replacer, is processed separately.

The method according to the invention can typically be carried out as follows.

Water is added to the pressed pulp before the jet cooking. In this manner the slurry can be easily pumped to the jet cooker. After jet cooking the enzymatic reaction is carried out at 50° C. in a tank with good stirring. In this manner the reaction time may be kept as low as possible. The enzymatic reaction is carried out after having adjusted the acidity to pH 5.0.

The preservation to a product with microbial stability can be carried out as follows. A separation of the reaction mixture by means of a decanter centrifuge is carried out before the evaporation step. In this manner the concentration step is not inhibited by reduced capacity due to particulate material, e.g. fibres, which can generate deposits on the calandria tubes of the evaporator or on membranes for ultrafiltration or hyperfiltration. The concentration is performed by means of a falling film evaporator. In this manner a dry matter content of above around 70% w/w of dry matter may be obtained. At this dry matter content the product is microbially stable. The concentration step may also be divided into two stages. First step may be a hyperfiltration (reverse osmosis) by means of tight membranes exclusively for removal of the water. Second step may be a final evaporation to ensure that such high dry matter content is reached at which the product is microbially stable. The above hyperfiltration step may be performed by means of a partly open membrane which allows a desalination. This may be wanted if the content of inorganic acids or salts is too high.

EXAMPLE 1

Jet cooking 40 kg of pressed potato pulp (10.9% dry matter) was mixed into 90 kg of tap water by means of a tank with stirring facilities. The homogenous slurry was jet cooked at 140° C. with a holding time of 20 seconds. The jet cooked slurry was hereafter cooled to 50° C. in a mantel cooled tank with stirring facilities.

The dry matter content of the jet cooked potato pulp was measured to 2.5% w/w.

To illustrate the effect of the jet cooking (the invention) in laboratory trials the following comparative trials have been carried out.

The pulp products (either the jet cooked or the not jet cooked pulp) were diluted with water until 2% dry matter in the following way: 136.4 g of jet cooked pulp was added to 33.6 g of water. In the laboratory this was the mixture with the highest dry matter concentration which was able to be stirred efficiently. The pH value of the pulp was around 6. For this trial pH was adjusted to 4.5 by means of 6N HCl. The cell wall degradation enzyme preparation SP-249 (Novo Enzyme information IB 297f-GB) was added from a diluted solution in the amounts equivalent to 0; 0.5; 1; 0.5; 1.0; 2.0; 4.0; and 8% w/w dry matter of enzyme preparation to potato pulp dry matter. The reaction temperature was 45° C. and the reaction time was 4 hours.

After enzyme reaction the mixtures were cooled in ice water. Then 150 g was centrifuged by means of a Labofuge centrifuge from Heraeus at 3000 x g (equivalent to 4000 rpm on the used centrifuge) for 15 minutes.

The centrifugates were collected, weighed and analyzed for dry matter content (oven, 105° C. over night).

The contents of sediments (amount of solids phase) were calculated on the basis of weight differences.

Calculations:

% soluble dry matter (abbreviated SDM %)=

(HC-E×HE)/HR/R×100%, where

HC=% dry matter of the centrifugate

E=ME/M (ME=gram of enzyme product, M=gram of reaction mixture).

HE=dry matter content of enzyme product

HR=dry matter content of raw material

R=MR/M (MR=gram of raw material used)

Results:

| E/HR % | % soluble dry matter | | % sediments | |
|---|---|---|---|---|
| | jet cooked | Untreated | Jet cooked | Untreated |
| 0 | 37.2 | 18.9 | 58.0 | 83.4 |
| 0.5 | 76.0 | 48.2 | 23.5 | 24.4 |
| 1.0 | 78.6 | 50.3 | 20.1 | 24.8 |
| 2.0 | 81.3 | 55.1 | 19.9 | 24.1 |
| 4.0 | 86.1 | 59.4 | 19.6 | 19.7 |
| 8.0 | 93.6 | 59.0 | 17.4 | — |

The above table is further illustrated in FIG. 1.

EXAMPLE 2

To illustrate the supporting effect of cellulase during the enzymatic degradation process of the jet cooked potato pulp in laboratory scale the following comparative trials have been carried out.

The pulp products (either the jet cooked or the not jet cooked pulp) were diluted with water until 2% dry matter in the following way: 136.4 g of jet cooked pulp was added to 33.6 g of water. In the laboratory this was the mixture with the highest dry matter concentration which was able to be stirred efficiently. The pH value of the pulp was around 6. For this trial pH was adjusted to 5.0 by means of 6 N HCl. The cell wall degradation enzyme preparations SP-249 and Celluclast® 1.5 L (Product sheet Novo Enzyme Process Division B 153h-GB) produced by Novo Nordisk was added from a diluted solution of each enzyme product in the amounts equivalent to 0; 0.25; 0.5; 1.0; 2.0; and 4.0% w/w dry matter of each enzyme preparation to potato pulp dry matter. Equal amounts of the two enzymes were added, calculated as dry matter. The reaction temperature was 45° C. and the reaction time was 4 hours.

After enzyme reaction the mixtures were cooled in ice water. Then 150 g was centrifuged by means of a Labofuge centrifuge from Heraeus at 3000 x g (equivalent to 4000 rpm on the used centrifuge) for 15 minutes.

The centrifugates were collected, weighed and analyzed for dry matter content (oven, 105° C. over night).

The content of sediments (amount of solids phase) were calculated on the basis of weight differences.

Calculations:

% soluble dry matter (abbreviated SDM %)=

(HC-E×HE)/HR/R×100%, where

HC=% dry matter of the centrifugate

E=ME/M (ME=gram-of enzyme product, M=gram of reaction mixture).

HE=dry matter content of enzyme product

HR=dry matter content of raw material

R=MR/M (MR=gram of raw material used)

Results:

| | % soluble dry matter | | % sediments | |
|---|---|---|---|---|
| E/HR % (each) | SP-249 | SP-249 + Celluclast | SP-249 | SP-249 + Celluclast |
| 0 | 39.3 | 38.8 | 57.7 | 46.1 |
| 0.25 | 64.0 | 68.1 | 23.6 | 18.2 |
| 0.5 | 67.6 | 74.9 | 22.7 | 15.2 |
| 1.0 | 68.2 | 80.2 | 20.8 | 12.3 |
| 2.0 | 70.9 | 85.6 | 16.7 | 9.6 |
| 4.0 | — | 86.8 | — | 7.7 |

Figure 2:
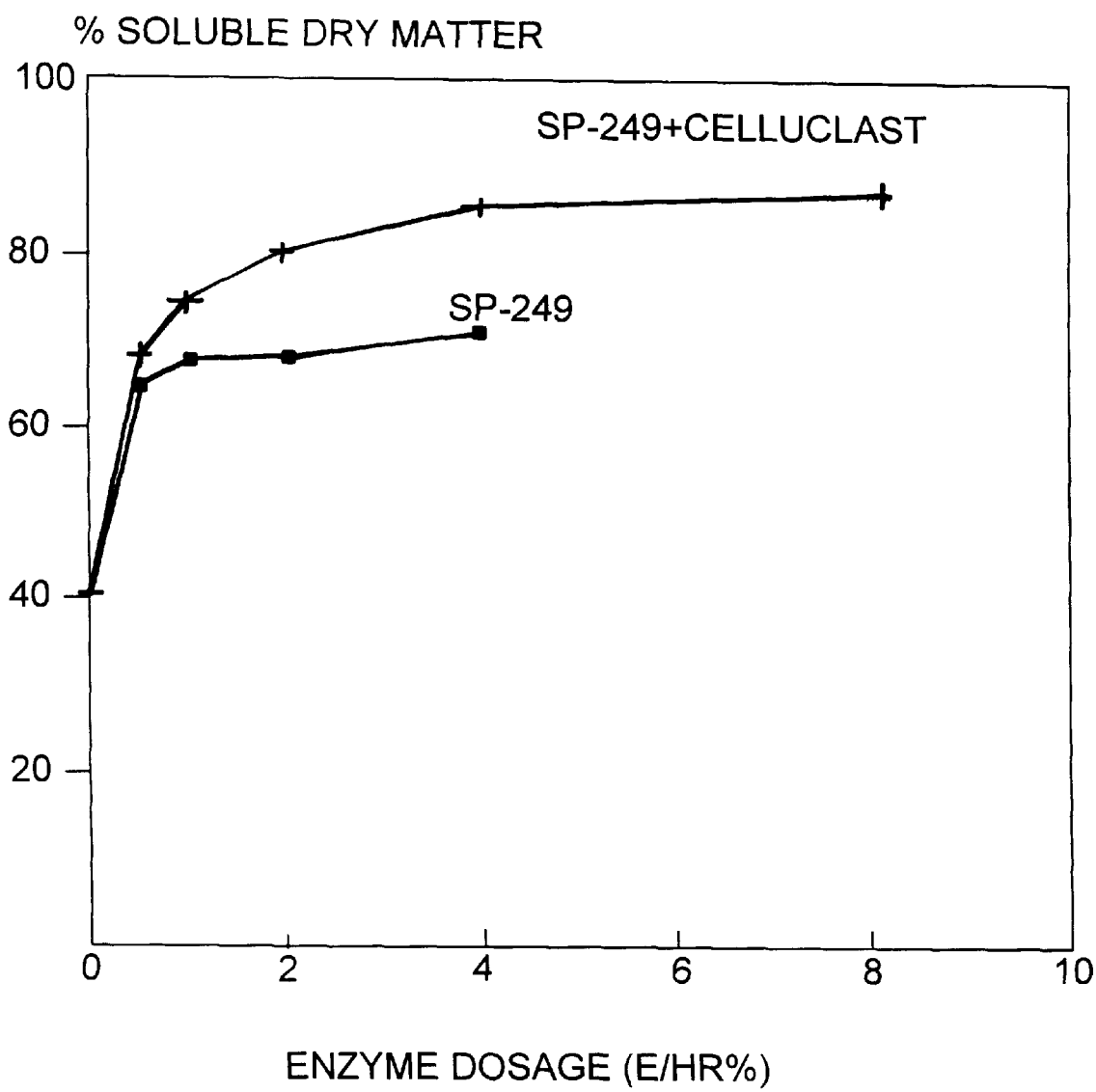
FIG. 2 shows percent soluble dry matter as a function of enzyme dosage for jet cooked and untreated samples described in Example 2.
Figure 3:
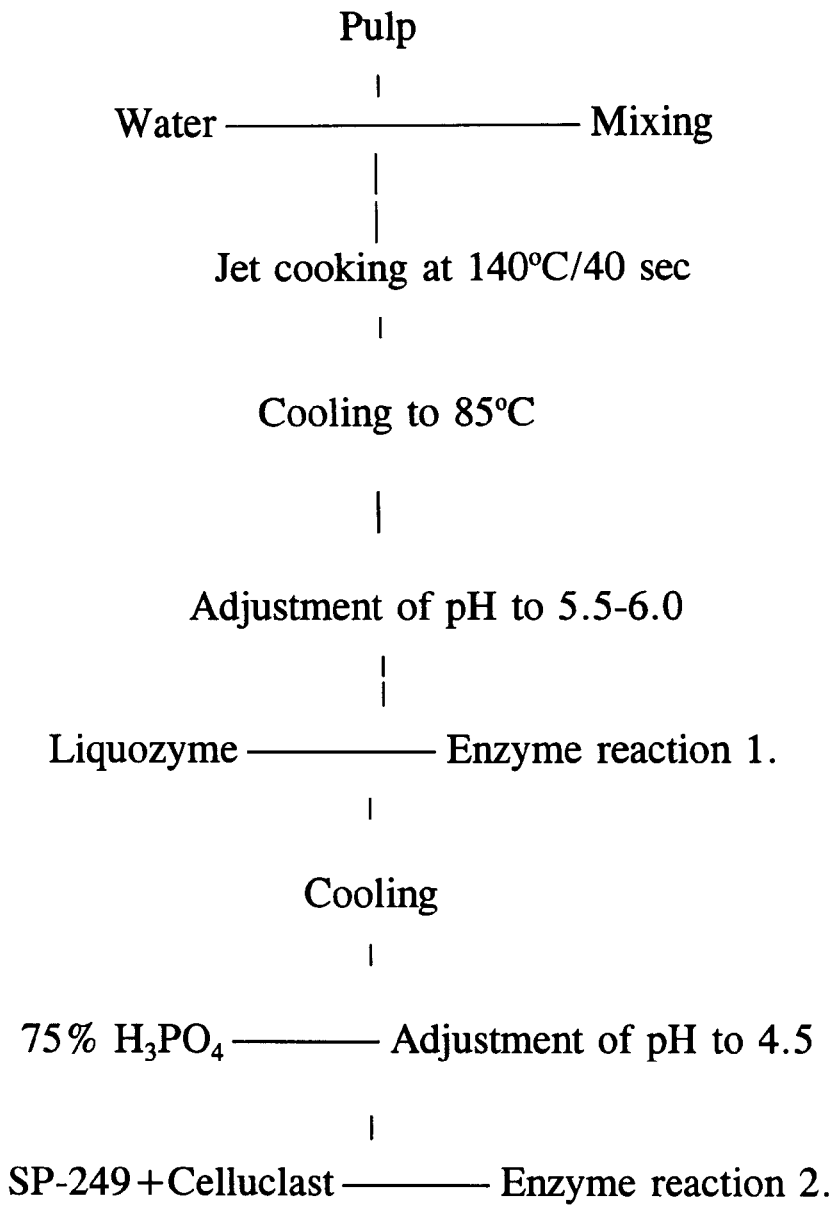
FIG. 3 illustrates the plan and flow diagram of Trial 4.1 as described in Example 4.
Figure 4:
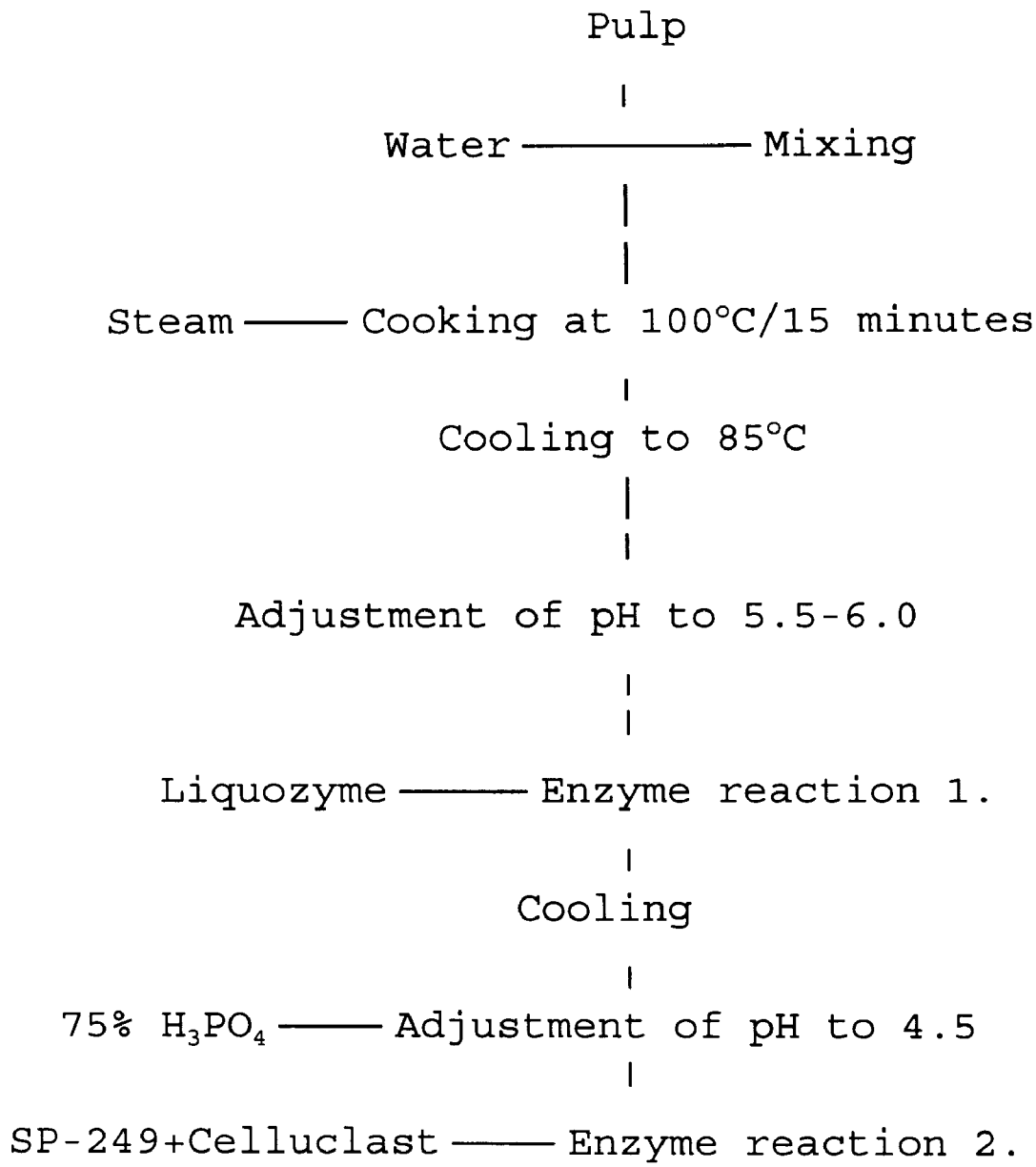
FIG. 4 illustrates the plan and flow diagram of Trial 4.2 as described in Example 4.

The above table is further illustrated in FIG. 2.

EXAMPLE 3

To illustrate the finally developed process in pilot plant scale the following procedure has been carried out:

150 kg of pressed potato pulp (10.9% dry matter) was mixed into 337.5 kg of tap water by means of a 500 liter tank with stirring facilities. The homogenous slurry was jet cooked at 140° C. with a holding time of 20 seconds. The jet cooker was Series M104MS Hydroheater, manufactured by Hydro-Thermal Corporation. Steam with a pressure of 12 bar was used. The flow of pulp slurry to the jet cooker was 300 liters/hour. The jet cooked slurry was subsequently cooled to 50° C. in a mantel cooled 1000 liter tank with stirring facilities. After the jet cooking the volume was 563 liters. The substrate concentration was 3.05% w/w dry matter and the contents of sediments, measured as in Example 1 or 2, was found to be 35–37% v/v.

The pH value was adjusted to 5.0 by means of 640 ml of 6.0 N HCl. 100 grams of the enzyme preparation SP-249 and 77.5 grams of Celluclast® 1.5 L was added. The enzyme reaction was carried out for 1.5 hours. After the reaction pH was found to be 4.48 and the volume of sediments was 19% v/v.

The concentration to microbial stability is carried out as follows. Separation by means of a 42 micron vibrating sieve was tried without success, because the particle size of the residual sediments was too small, 25 liter of reaction mixture being lost by this trial. Hereafter a separation was performed by means of a decanter centrifuge of the type Alfa Laval NX 310B-31 at 3250 rpm. The feed flow was 600 liters/hour. 538 liters of centrifugate were collected. It contained 1.5% w/w dry matter; the contents of sediments were 1.5% v/v. The solids from the decanter exhibited a clay like consistency. Approximately 25 kg were collected.

The centrifugate was evaporated on a Niro Atomizer, type FF200 vacuum, falling film evaporator at a concentrate temperature of 70° C. at 0.75 bar. The evaporating capacity was 165–190 liters of $H_2O$ per hour. 44 liters of concentrate with 28.5 °Brix were collected. The final concentration was performed on a LUWA rotating film evaporator, also used at 70° C. 15 liters of a concentrate with 65.1 °Brix were collected. The evaporation capacity was around 60 liters of $H_2O$/hour.

The concentrate and the solids from the decanter was mixed. This mixture was spray dried with an inlet temperature of 235–245° C. and an outlet temperature of 90–95° C. 10 kg of spray dried powder was collected.

The composition of the spray dried product was estimated to

94% of dry matter

10% of protein

70% of carbohydrates

EXAMPLE 4

In order to illustrate that the method according to the invention can be performed with a batch cooking process and with a jet cooking process as well the following comparative trials have been carried out.

Liquozyme® is an alpha-amylase preparation; SP-249 is a preparation of the cell wall degrading enzyme SPS-ase, and Celluclast is a cellulase preparation.

Procedure 300 kg of pressed potato pulp was mixed with 375 liters of tap water in a tank with stirring facilities. The homogenous slurry was jet cooked in the Hydroheater® referred to in Example 3, at 140° C. and with a holding time of 40 seconds. The jet cooked slurry was subsequently cooled to 85° C. in a tank with mantle cooling. The volume after the jet cooking was 800 liters and the dry matter content of the substrate was 6.56%.

pH was now adjusted to 5.7 by means of 5.8 liters of 5 N NaOH. 264 g of Liquozyme® was added. An enzyme reaction was carried out for 120 minutes at 85° C. During the reaction samples were taken for a centrifugation test. Measurements of °Brix and osmolality of the liquid phase and of the volume of the solid phase were made. Data are shown in the tables below.

The temperature of the reaction mixture was now adjusted to 50° C. and pH of the amylase treated pulp was now adjusted to 4.5 by means of 2 liters of 75% $H_3PO_4$. 262 g of Celluclast® 1.5 L and 262 g of SP-249 was added. An enzyme treatment was now carried out for 240 minutes. Measurements of °Brix, osmolality and pH of the liquid phase and the volume of the solid phase was made. Data are shown in the tables below.

Procedure 43.5 kg of pressed potato pulp was mixed with 70 liters of tap water in a tank with stirring facilities. The homogenous slurry was heated by addition of live steam and by heating of the mantle to 100° C. for 15 minutes. The cooked slurry was subsequently cooled to 85° C. in the tank with cooling water in the mantle. The volume after the cooking was 120 liters and the dry matter content of the substrate was 5.8%.

pH was now adjusted to 5.9 by means of 0.3 liters of 5 N NaOH. 35 g of Liquozyme® was added. An enzyme reaction was carried out for 80 minutes at 85° C. During the reaction samples were taken for, a centrifugation test. Measurements of °Brix and osmolality of the liquid phase and of the volume of the solid phase were made. Data are shown in the tables below.

The temperature of the reaction mixture was now adjusted to 50° C. and pH of the amylase treated pulp was now adjusted to 4.5 by means of 0.3 liters of 75% $H_3PO_4$. 35 g of Celluclast® 1.5 L and 35 g of SP-249 was added. An enzyme treatment was now carried out for 240 minutes. Measurements of °Brix, osmolality and pH of the liquid phase and of the volume of the solid phase were made. Data are shown in the tables below.

Trial 4.1 with jet cooking

| Time minutes | ° Brix | Osmolalty increase | pH | % Sludge |
|---|---|---|---|---|
| Treatment with alpha-amylase: | | | | |
| 0 | 4.1 | 0 | no data | — |
| 10 | 4.1 | 19 | | — |
| 30 | 4.1 | 21 | | — |
| 60 | 4.2 | 21 | | 47 |
| 95 | 4.2 | 23 | | 47 |
| 120 | 4.4 | 28 | | — |
| Treatment with Celluclast ® and SP-249: | | | | |
| 0 | 4.4 | 0 | 4.50 | 51 |
| 30 | 4.6 | 27 | 4.49 | 41 |
| 45 | 4.7 | 21 | 4.49 | 41 |
| 75 | 4.8 | 39 | 4.49 | 35 |
| 105 | 4.9 | 45 | 4.49 | 35 |
| 135 | 4.9 | 52 | 4.47 | 30 |
| 180 | 4.9 | 68 | 4.45 | 31 |
| 240 | 5.1 | 83 | 4.44 | 29 |

Trial 4.2 with simple steam cooking

| Time minutes | ° Brix | Osmolalty increase | pH | % Sludge |
|---|---|---|---|---|
| Treatment with alpha amylase: | | | | |
| 5 | 3.2 | 3 | no data | 44 |
| 10 | 3.3 | 6 | | 44 |
| 20 | 3.3 | 8 | | 45 |
| 45 | 3.4 | 6 | | 42 |
| 60 | 3.5 | 6 | | 42 |
| 80 | 3.5 | 6 | | 42 |
| Treatment with Celluclast ® and SP-249: | | | | |
| 2 | 3.8 | 2 | 4.50 | 42 |
| 15 | 4.1 | 13 | | 35 |
| 30 | 4.3 | 30 | | 33 |
| 60 | 4.3 | 36 | | 30 |
| 90 | 4.4 | 39 | 4.38 | 29 |
| 120 | 4.4 | 49 | 4.37 | 30 |
| 150 | 4.5 | 50 | 4.37 | 30 |
| 180 | 4.6 | 65 | 4.37 | 29 |
| 210 | 4.6 | 63 | 4.36 | 29 |
| 240 | 4.6 | 63 | 4.36 | 29 |

By comparison of the two tables it can be concluded that both cooking procedures are operable in relation to the method according to the invention with a slight preference for the jet cooking.

I claim:

1. A method of making an animal fodder stabilized against microbial degradation, comprising:

(a) jet-cooking potato pulp at a temperature of between about 125° C. and 140° C. for between about 20 to 100 seconds;

(b) cooling the jet-cooked potato pulp; and (c) adding a cell-wall degrading enzyme to the cooled potato pulp in order to enzymatically degrade the cell walls in the potato pulp, wherein a fodder stabilized against microbial degradation is produced.

2. The method of claim 1 wherein said cell-wall degrading enzyme is SPS-ase.

3. The method of claim wherein said enzymatically degraded product of step (c) is preserved by concentrating and subsequently spray drying to form a concentrate with a water content of less than 5%.

4. The method of claim 3 wherein the concentrate, immediately before spray drying, is mixed with potato fruit water which has been jet cooked, enzyme treated and concentrated.

5. The method of claim 3 wherein the enzymatically degraded product of step (c), prior to concentrating, is subjected to ultrafiltration by means of ultrafiltration equipment with a cut off value of around 20,000 daltons.

6. The method of claim 1, wherein the cell-wall degrading enzyme is one or more of cellulase, hemicellulase, and SPS-ase.

* * * * *